United States Patent [19]
Tens et al.

[11] Patent Number: 5,437,987
[45] Date of Patent: Aug. 1, 1995

[54] TRIPLE GRADIENT PROCESS WITH ANTIBODY PANNING TO RECOVER NUCLEATED FETAL CELLS FROM MATERNAL BLOOD

[75] Inventors: Nelson N. H. Teng, Millsborough; Marcia Bieber, Los Altos Hills; Neelima M. Bhat, Cupertino, all of Calif.

[73] Assignee: The Board of Trustees of the Leland Stanford Junior University, Stanford, Calif.

[21] Appl. No.: 77,295

[22] Filed: Jun. 14, 1993

Related U.S. Application Data

[63] Continuation-in-part of Ser. No. 951,628, Sep. 25, 1992, Pat. No. 5,275,933.

[51] Int. Cl.$^6$ ............................................. G01N 33/53
[52] U.S. Cl. ................................. 435/7.25; 435/2; 436/518; 436/526; 436/531; 436/811
[58] Field of Search ................... 435/2, 7.25; 436/518, 436/526, 531, 811; 210/789

[56] References Cited

U.S. PATENT DOCUMENTS

| | | | |
|---|---|---|---|
| 3,852,194 | 12/1974 | Zine, Jr. ........................ | 210/83 |
| 4,147,628 | 4/1979 | Bennett et al. ................ | 210/83 |
| 4,153,739 | 5/1979 | Kessler ........................... | 427/2 |
| 4,190,535 | 2/1980 | Luderer et al. ................ | 210/83 |
| 4,255,256 | 3/1981 | Ferrante et al. ............... | 210/730 |
| 4,350,593 | 9/1982 | Kessler .......................... | 210/516 |
| 4,675,286 | 6/1987 | Calenoff ........................ | 435/7 |
| 4,751,001 | 6/1988 | Saunders ....................... | 210/516 |
| 4,822,745 | 4/1989 | Burns et al. ................... | 436/63 |
| 4,925,786 | 5/1990 | Uthemann ..................... | 435/7.25 |
| 4,927,750 | 5/1990 | Dorn .............................. | 435/2 |

FOREIGN PATENT DOCUMENTS

WO91/14768 10/1991 WIPO .

OTHER PUBLICATIONS

Bhat et al, "One step separation of human fetal lymphocytes from nucleated redblood cells", in J. of Immunol. Methods v. 131 (1990) pp. 147–149.

Bhat et al, "One step enrichment of nucleated red bloods cells" in J. of Immunol. Methods, v. 158 (1993) pp. 277–280.

Okada et al, "Glycolipid antigens with Blood Group I and i specificities from Human Adult and Umbilical Cord Erythrocytes" in J of Immunology, v. 133, No. 2 (Aug. 1984) pp. 835–842.

Bianchi et al; Direct Hybridization to DNA from Small Numbers of Flow-Sorted Nucleated Newborn Cells, Cytometry 8: pp. 197–202 (1987); (Received for Publi Aug. 8, 1986, accepted Oct. 22, 1986.

Iverson et al; Detection and Isolation of Fetal Cells from Maternal Blood Using the Flourescence-Activated Cell Sorter (FACS), Prenatal Diagnosis, vol. 1, pp. 61–73 (1981).

Herzenberg et al; Fetal Cells in the Blood of Pregnant Women: Detection and Enrichment by Fluorescence-Activated Cell Sorting Proc. Natl. Acad. Sci USA, vol. 76, No. 3 pp. 1453–1455, Mar. 1979.

Bianchi et al; Isolation of Fetal DNA from Nucleated Erythrocytes in Maternal Blood Proc. Natl. Acad. Sci. USA, vol. 87 pp. 3279–3283, May 1990 Medical Sciences.

Corash et al; Separation of Erythrocytes According to Age on a Simplified Density Gradient J. Lab. Clin. Med, Jul. 1974, vol. 84 No. 1, pp. 147–151.

*Primary Examiner*—Carol A. Spiegel
*Attorney, Agent, or Firm*—Oblon, Spivak, McClelland, Maier & Neustadt

[57] ABSTRACT

A method for separating nucleated fetal red blood cells and nucleated fetal cells and maternal granular sites from maternal blood is achieved by applying maternal blood to a triple gradient gel, isolating nucleated fetal cells from the gel and binding the isolated fetal cells to a solid support by means of an anti-i antibody bound to the solid support. The separated fetal cells can then be subjected to analysis for fetal sex or genetic disorders.

9 Claims, No Drawings

TRIPLE GRADIENT PROCESS WITH ANTIBODY PANNING TO RECOVER NUCLEATED FETAL CELLS FROM MATERNAL BLOOD

RELATED APPLICATION

This application is a Continuation-in-Part application of U.S. application Ser. No. 07/951,628, filed Sep. 25, 1992, now U.S. Pat. No. 5,275,933.

BACKGROUND OF THE INVENTION

1. Field of the Invention

The present invention relates to a method for separating nucleated fetal red blood cells and other nucleated fetal cells from maternal blood using a triple gradient gel and antibody panning.

2. Discussion of the Background

The examination of fetal cells for early detection of fetal diseases and genetic abnormalities is undertaken in approximately one out of every thirty pregnant women. The main indication is maternal age (over 35 years). The tests may involve DNA gene typing or, more commonly, the use of live fetal cells for chromosomal karyotyping.

Fetal cells are usually obtained by amniocentesis, the removal of amniotic fluid from the amniotic cavity within the amniotic sac or placenta. The procedure presents a risk of harm to the fetus, particularly after the first trimester of pregnancy. The risk to the fetus together with the high cost of the procedure have prevented the establishment of examination of fetal cells for early detection of abnormalities as a routine procedure in pregnancy.

In the late 1970's and early 1980's, Herzenberg and his colleagues reported that fetal cells were present in maternal blood as early as 15 weeks gestation. Maternal and fetal cells were separated using fluorescence-activated cell sorting (FACS) by staining maternal blood for a distinguishing paternal HLA antigen. To date, the technique has not been successfully adapted for use as a clinical technique for either karyotyping or fetal DNA analysis.

Fetal cells present in maternal blood have been used to perform analysis of genes present in the fetus. In one technique, the maternal and fetal cells were not separated and the DNA from the cell mixture is amplified with Y chromosome-specific primers to determine whether the fetus is male. It has been suggested that DNA amplification techniques can also be performed to detect gene sequences associated with disease in this manner. Of course, the method cannot be used where the mother is a carrier for the trait.

To date, amniotic fluid has been the only source of antenatal cells to provide a sufficient number of live cells for karyotyping. Furthermore, DNA analysis methods have only been possible in relatively limited situations which depend on particular differences in maternal and fetal cells, e.g. presence of the Y chromosome in the fetus or presence of HLA-A2 antigen on fetal, but not maternal, cells.

Herzenberg and his colleagues have described methods for separating maternal and fetal cells in maternal blood using fluorescence-activated cell sorting (FACS). In Herzenberg et al, *Proc. Natl. Acad. Sci. USA* 76:1453–1455 (1979), cells in blood samples from 15-week pregnant HLA A2-negative women were stained for HLA A2 antigen. Stained cells were separated by FACS and collected to enrich the population of fetal cells. Although the technique was demonstrated to effectively identify male, HLA A2-positive cells in maternal blood, to date the technique has not been successfully adapted for general applicability.

In Iverson et al, *Prenat. Diag.* 1:61–73 (1981), peripheral blood lymphocytes (PBLs) from either 15 week or 21 to 25 week pregnant women were examined. If the woman was HLA A2-negative, her cells were stained with anti-HLA A2 reagents, sorted by FACS onto microscope slides (for fetuses who were HLA A2-positive), stained with quinacrine and examined microscopically for Y chromatin-positive cells.

Bianchi et al, *Cytometry* 8:197–202 (1987) report a technique that allows direct hybridization to the DNA of cells which were flow sorted onto nitrocellulose filters which eliminates the need for a DNA isolation step. The method was performed on human cord blood. The technique is reportedly useful in situations where there is a limited amount of DNA available for analysis such as for fetal cells recovered from maternal blood.

U.S. Pat. No. 4,675,286 describes a method for obtaining fetal cells for diagnostic examination in which detached cells from the uterine cavity and outer surface of the amniotic sac are incubated with a separation antibody which binds preferentially to either fetal or maternal cells. The antibody can be bound to an insoluble support or conjugated with a fluorescent label and removed with a cell sorter to effect separation.

Albright et al, *Cytometry* 7:536–543 (1986) describe the use of centrifugal separation of cells in sputum specimens as an alternative to flow cytometry.

*Society for Clinical Cytology* 1988 Abstracts p.6 describe in situ hybridization for detection of structural and numerical abnormalities using nonradioactive probes for detection of aneuploidy and translocations (Pinkel et al, No. 13). Commercial probes are available for chromosomes 13, 18 and 21.

Density gels and centrifugation are routinely used to separate certain populations or subpopulations of blood cells from adult blood. A variety of these methods including use of a one step density gradient are summarized in U.S. Pat. No. 4,255,256, for example. In these methods, the cell mixture is placed on the surface of a gel in a tube, and the components are settled into layers by gravity or centrifugation. Single density gradient gels generally yield two zones, one at the surface of the gel and the other at the bottom. Continuous density gradient gels yield zones of cells throughout the gel separated by density. The patent also describes discontinuous density gradients with two or more separating solutions of different densities layered on top of one another. The densities are selected to provide a discontinuous gradient over a desired range. In the procedures, nucleated cells such as lymphocytes are usually collected as a mixture separated from mature red blood cells.

Each of the above-described references and the publications cited therein are hereby incorporated by reference into this application.

SUMMARY OF THE INVENTION

It is an object of this invention to provide a source of fetal cells for chromosome and DNA analysis for genetic defects and diseases which does not expose the mother or the fetus to the medical risks of sample collection from the placenta or amniotic fluid.

It is another object of this invention to provide a method for separating nucleated fetal cells from maternal blood which can be carried out as a simple routine by laboratory technicians.

The method of this invention for separating nucleated fetal red blood cells from maternal blood mononuclear cells, granulocytes and mature red blood cells (RBCs) comprises applying maternal blood to a discontinuous gradient gel having at least first, second, and third layers. The first and second layers and the second and third layers form a first and a second interface therebetween, respectively. The first layer has a density in the range of from about 1.115 to about 1.125 g/ml. The second layer has a density in the range of from about 1.105 to about 1.110 g/ml. The third layer has a density in the range of from about 1.075 to about 1.085 g/ml. The gel is subjected to separation forces such as gravity or centrifugation for a time sufficient to cause movement of nucleated fetal red blood cells to the first, upper interface and maternal granulocytes and nucleated fetal cells to the second, lower interface. The nucleated fetal cells can then be removed from the respective interface.

After the nucleated fetal cells have been concentrated by the triple gradient gel process, the fetal cells are bound to a solid support through antigen-antibody binding with an IgM antibody bound to the solid support. The IgM antibody of the present invention has anti "i" specificity, i.e., recognizes an epitope on an unbranched repeating type 2 N-acetyl lactosamine chain. A solid support having the IgM antibodies bound thereto is placed in contact with the isolated fetal cells to allow antigen-antibody binding of the antibody to the fetal cells. Non-adherent cells are washed from the solid support. The adherent fetal cells can then be fixed and subjected to analysis to determine genetic defects such as trisomies or other genetic defects using commercially available fluorescent in situ hybridization processes. Alternatively, the adherent cells can be released from the solid support by warming and then fixed to a slide by centrifugation and processed for PCR or other procedures.

DETAILED DESCRIPTION OF THE PREFERRED EMBODIMENTS

The terms "first layer", "second layer" and "third layer" as used herein, are defined to identify the order of layers in the direction of the separating force, from most force to least force, the first layer being below the second layer in the force field. In a gravity separation process, the first layer is positioned below the second layer which is, in turn, below the third layer. In a centrifugal separation process, the second layer is positioned between the axis of spin and the first layer, and the third layer is positioned between the axis of spin and the second layer.

The present method is designed to recover fetal cells present in a maternal blood sample, particularly a venous blood sample. Preferably, the pregnant woman is late in her first trimester or in her second trimester of pregnancy. A particularly preferred time is 12-16 weeks gestation. The sample can be any blood sample which is prevented from clotting such as a sample containing heparin or ACD (acid citrate dextrose) solution. The sample can be stored at room temperature, but should be used the same day to minimize dead cells and cell debris. The number of fetal cells in the sample varies depending on factors including the age of the fetus, number of fetal/maternal bleeds, the volume of blood in each episode, and the amount of time since the last bleed. Typically, from 7 to 30 ml of maternal blood provides sufficient fetal cells upon separation from maternal cells. Preferably, 20-30 ml or more blood is drawn to ensure sufficient cells without the need to draw an additional sample.

The method of this invention provides a method for isolating fetal cells from maternal blood, a method which does not expose the fetus to the risks of amniocentesis and villus biopsy sampling methods. It includes the steps of applying maternal blood to a discontinuous gel having the critical densities required to separate the target nucleated fetal red blood cells from maternal granulocytes, maternal blood mononuclear cells, mature red blood and other components in maternal blood and using a separation force such as gravity or centrifugal forge to effect the separation. The separated cells can be removed from the gel for further processing and analysis.

The discontinuous gel can be prepared by standard procedures from conventional gradient gel compositions, and neither the method of preparing the gel nor the gradient gel composition, per se, is a part of this invention. Suitable gel compositions and methods for preparing the gels are described in U.S. Pat. Nos. 4,255,256, 4,751,001, and 4,927,750, for example, and the entire contents of these patents are hereby incorporated by reference. FICOLL (polysucrose) compositions (Pharmacia Fine Chemicals, Sweden) are one type of suitable gel. These polymers are generally mixed with a compound which forms a high density, low viscosity aqueous solution such as the iodinated low molecular weight compounds such as sodium metrizoate or sodium diatrizoate. Alternatively, the cell separation can be effected with solutions of dextran or bovine serum albumin (BSA). Suitable density gradient gels formed from colloidal silica having a non-toxic organic coating are described in U.S. Pat. No. 4,927,750.

Other compositions which can be included are barrier phases which can be used to establish a barrier between lighter and heavier layers such as described in U.S. Pat. Nos. 4,190,535, 3,852,194, 4,147,628, 4,350,593 and 4,153,739, for example. The barrier phase gradients must allow cells to penetrate through the barrier and have physiologicosmolality.

The multiple layer, discontinuous density gradient gel can be constructed by conventional layering techniques wherein each density layer is successively applied, from the most dense on the bottom of a container to the least dense layer on the top. Conveniently, the most dense layer is added to the tube first.

The maternal blood can be collected at any stage during the pregnancy when it would normally contain nucleated fetal red blood cells. The cells are usually present after week 15 of pregnancy.

The maternal blood pretreated with heparin or another anticoagulant is preferably applied to the assembled gel layers, most preferably being applied to the top surface of the gel layers. However, the maternal blood can be applied to the bottom or at an intermediate level, if desired, since the blood components migrate in the separation force field to an interface with adjoining gel densities above and below the density of the blood component. Alternatively, the gradient layers can be sequentially added to maternal blood.

Nucleated fetal red blood cells will efficiently collect at an interface between a more dense layer and a less dense layer. The more dense layer has a density greater than that of nucleated fetal red blood cells but less than the density of granulocytes.

A system for simultaneously separating nucleated fetal red blood cells and nucleated fetal cells and maternal granulocytes from other maternal blood components would require at least first, second and third layers. The first and second layers form a first interface therebetween wherein nucleated fetal cells and maternal granulocytes collect. Maternal granulocytes will efficiently collect at an interface between a more dense layer and a less dense layer. In addition, the layer contains nucleated cells which are clearly fetal in origin. The cells may be fetal granulocytes or fetal trophoblast cells. The more dense layer has a density greater than that of the granulocytes but less than the effective density of mature red blood cells. The less dense layer has a density less than granulocytes but greater than nucleated fetal red blood cells. The second and third layers form a second interface therebetween wherein nucleated fetal red blood cells collect. As stated previously, nucleated fetal red blood cells will efficiently collect at an interface between a layer having a density greater than that of nucleated fetal red blood cells but less than the density of granulocytes and a layer having a density less than that of nucleated fetal red blood cells but greater than that of mononuclear cells.

It has been discovered that the first layer in such a combination should have a density in the range of from about 1.115 to about 1.125 g/ml. The second layer should have a density in the range of from about 1.105 to about 1.110 g/ml. When the density of the second layer was greater than 1.110 g/ml, noticeable contamination with granulocytes occurred. The third layer should have a density in the range of from about 1.075 to about 1.085 g/ml. Most preferred is the use of a gel having densities of 1.119, 1.107 and 1.077 g/ml for the first, second and third layers, respectively.

The gel layers are then exposed to a separation force field such as gravity or centrifugal force for a time sufficient to allow movement of the blood components to their respective densities. In the two layer system, the nucleated fetal red blood cells collect in the interface area, the granulocytes and mature red blood cells settling to the lowest level, and the maternal mononuclear cells collect at the highest level. In the three layer system, the nucleated fetal red blood cells collect at the middle interface, and nucleated fetal cells and maternal granulocytes collect at the lower interface.

The method of this invention can be easily carried out with conventional centrifuge tubes and laboratory centrifuges. The gels are then layered directly into a centrifuge tube, and the collected cells are removed from an intermediate layer by pipette, for example.

The collected cells are washed and suspended in a suitable physiologic solution. The suspension medium is a physiologic solution, such as a physiologic buffer, to maintain cell integrity and should contain calcium ions for good antigen-antibody binding. Most physiologic buffers, e.g. Tris buffer, phosphate buffer (PB), citrate buffer, phosphate buffered saline (PBS) are suitable. Balanced salt solutions such as Earle's balanced salt solution (EBSS), Hank's balanced salt solution (HBSS), and Gey's balanced salt solution (GBSS) are also suitable. Preferred solutions are HBSS and EBSS.

The suspended cells are then used for panning. By the term "panning" is meant binding the nucleated fetal cells to a solid support through an antigen-antibody complex with a cold agglutinin antibody having anti "i" specificity bound to the solid support. It has now been discovered that an antibody, preferably IgM, having anti "i" specificity is capable of binding to N-acetyl lactosamine chains on the surface of nucleated fetal cells. This antibody specificity allows one to bind fetal cells to the surface of the solid support through an antigen-antibody binding complex with the antibody.

Cold agglutinin antibodies are well-known in the art. The term "cold agglutinin" is used to describe human autoantibodies which agglutinate red blood cells at low temperature. Cold agglutinin antibodies can be isolated from numerous mammal species including humans. Low-titer cold agglutinins can be demonstrated in almost all sera of adults. Two major classifications of antigenic specificity among cold agglutinins are anti-I specificity and anti-i specificity. Anti-I cold agglutinins recognize antigens fully expressed only on adult red blood cells. Anti-i cold agglutinins recognize antigens expressed primarily on newborn red blood cells. Both adult and newborn red blood cells lack a nucleus. This invention includes the discovery that anti-i antibodies also bind to nucleated fetal red blood cells. Anti-i antibodies recognize a linear epitope made up of repeating N-acetyl lactosamine units having the structure shown below.

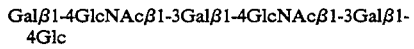

Galβ1-4GlcNAcβ1-3Galβ1-4GlcNAcβ1-3Galβ1-4Glc

The specificity of anti-i antibodies is well-known and has been thoroughly characterized. See Roelcke, *Transfusion Medicine Reviews*, volume III, no. 2 (April), 1989, pp. 140–166 and Pruzanski et al, *Clinical Immunology Reviews*, 3(1), 131–168 (1984). Any known anti-i antibody binding the linear epitope shown above can be used in the present invention and bound to the solid support. Specific anti-i antibodies can be produced by hybridomas prepared from splenocytes isolated from patients with cold agglutination disease and characterized as anti-i antibodies according to known and described methods. See for example Pascual et al, *J. Immun.*, 146(12), 4385–4391 (1991) (FS-1, FS-2 antibodies); Niemann et al, *Biochem. Biophys. Res. Comm.*, 81(4), 1286–1293 (1978) (anti-i Dench, anti-i Hog, anti-i McC antibodies); Pascual et al, *J. Immun.*, 149(7), 2337–2344 (1992) (FS-1, FS-2 antibodies); and Grillot-Courvalin et al, *Europ. J. Immun.*, 22:1781 (1992) (HY18, anti-i DEN antibodies). Other suitable anti-i antibodies include antibodies 216 and A6(H4C5) produced as described below.

Procedures for binding antibodies to insoluble supports are described in U.S. Pat. Nos. 3,551,555, 3,553,310, 4,048,298 and RE-29,474, for example, all of which are incorporated herein in the entirety. Binding of antibodies to polystyrene by adsorption has been described in U.S. Pat. Nos. 3,646,346 and 4,092,408, for example. These processes may be used to bind the anti-i antibody to the solid support.

A variety of materials can be used as the insoluble support, the most important factor being the binding of the primary antibody to the surface, the absence of interference with the conjugation reactions or with other reactions which can be employed to determine the presence and extent of the conjugating reaction. Organic and inorganic polymers, both natural and synthetic, can be used as the insoluble support.

Examples of suitable polymers include polyethylene, polypropylene, polybutylene, poly(4-methylbutylene), butyl rubber, silastic polymers, polyesters, polyamides, cellulose and cellulose derivatives, such as cellulose acetate, nitrocellulose and the like, acrylates, methacrylates, vinyl polymers, such as polyvinyl acetate, polyvinyl chloride, polyvinylidene chloride, polyvinyl fluoride, and the like, polystyrene and styrene graft copolymers, rayon, nylon, polyvinylbutyrate, polyformaldehyde, for example. Other materials which can be used as the insoluble support can be the latexes of the above polymers, silica gel, silicon wafers, glass, paper, insoluble protein, metals, metalloids, metal oxides, magnetic materials (magnetic beads), semi-conductive materials, cermets and the like.

A preferred diagnostic support entails a polystyrene or styrene copolymers such as styrene-acrylonitrile copolymers, or polyolefins such as polyethylene or polypropylene, and acrylate and methacrylate polymers and copolymers. The primary antibody can be coordinated or bound to the insoluble support by adsorption, ionic bonding, van der Waals adsorption, electrostatic bonding, or other non-covalent bonding, or it can be bound to the insoluble support by covalent bonding. Preferred forms of insoluble supports are beads, microwells and dipsticks.

The fetal cells suspended in physiologic solution are contacted with the IgM antibodies bound to the solid support, thereby causing the fetal cells to adhere to the solid support through an antigen-antibody binding complex. The fetal cell suspension and the solid support having bound antibody are contacted for a sufficient time to allow formation of the antigen-antibody complex. Generally, contact times ranging from about 1-4 hours, preferably about 1-2 hours, at temperatures of about 0°-10° C., preferably about 4° C., are sufficient to allow cells to settle and allow formation of the antigen-antibody complex. Non-adherent cells can be removed from the solid support by gentle rinsing with cold physiologic solution.

After washing with cold physiologic solution, e.g. PBS, to remove non-adherent cells, the solid support may be warmed to about 37° C. to release the bound fetal cells from the support. These cells are then concentrated and processed for conventional in situ hybridization or PCR. For example, the fixed cells can then be probed for genetic defects or probed to determine fetal sex using known methods. The fetal cells can be used in the same manner as fetal cells obtained by other methods such as amniocentesis and chorionic villus biopsy. The cells can be used as a source of DNA for analysis of the fetal alleles, as by polymerase chain reaction (PCR) amplification. PCR analysis methods have been used to detect, for example, fetal sex, β-thalassemia, phenylketonuria (PKU), and Duchenne's muscular dystrophy.

In one embodiment of the present invention, the solid support with bound fetal cells is warmed to release the bound fetal cells from the support as described above. The released fetal cells can then be fixed to a glass support, e.g., a microscope slide, and subjected to fluorescence in situ hybridization (FISH) using known fluorescent DNA probes. FISH DNA probes are commercially available and may be used with the process of the present invention using known in situ hybridization techniques. Typically, the fetal cells are suspended in a solution of KCl and incubated at 37° C. for several minutes. After centrifugation, the resulting pellet is resuspended in a mixture of methanol/glacial acetic acid (3:1, v:v) and again centrifuged. The resulting pellet is resuspended in the supernatant and transferred to a slide for FISH using commercially available fluorescent DNA probes for specific chromosomes, i.e., chromosomes 18, 21, etc.

This invention is further illustrated by the following specific but non-limiting examples. Temperatures are given in degrees Centigrade and concentrations as weight percent unless otherwise specified. Procedures which are constructively reduced to practice are described in the present tense, and procedures which have been carried out in the laboratory are set forth in the past tense.

EXAMPLES

Example 1

1,000 fetal nucleated cells from 16 week old fetal liver were added to 30 ml of heparinized adult whole blood and mixed. This produces a ratio of one fetal cell per $5 \times 10^8$ to $1 \times 10^9$ red blood cells which is approximately the same ratio found in pregnant women.

After dilution with two parts PBS, the blood was carefully layered onto a discontinuous, triple gradient with HISTOPAQUE-1119 (FICOLL and sodium diatrizate; Sigma Diagnostics) at the bottom as the first layer, a gradient material having a density of 1.107 g/ml in the middle as the second layer (prepared by mixing HISTOPAQUE solutions) and HISTOPAQUE-1077 (FICOLL and sodium rizate; Sigma Diagnostics) (1 ml each) at the top as the third layer in 15 ml sterile polystyrene tubes.

The tubes were centrifuged at $700 \times g$ for 30 minutes. The cells at all gradient interfaces were recovered, washed twice with PBS and resuspended in HBSS with 2% fetal calf serum (FCS).

Examination of the samples showed that in the three layer gradient gel system, mononuclear cells collected on the top surface, the nucleated fetal red blood cells collected at the interface between the second and third gel layers. Some nucleated cells of fetal origin and all maternal granulocytes collected at the interface between the first and second layers and the mature red blood cells collected at the bottom of the tube.

Purified IgM antibody (216) with an anti "i" specificity obtained as described below (0.5 ml at a concentration of 10–20 micrograms/ml), was incubated overnight at 4° C. in a $35 \times 10$ mm plastic tissue culture dish. When ready for use, the dish was washed with 10% FCS in PBS and incubated 30 minutes with 10% FCS to block reactive plastic sites and then washed again. The cells from the triple gradient enrichment described above were added to the dish and incubated for 1.5 hours at 4° C. Non-adherent cells were removed by gently rinsing the dish with cold PBS and the dish was kept cold by sitting on an ice pack or on a refrigerated plate.

To determine that the adherent cells after panning were fetal cells, the adherent cells were fixed by washing with ethanol and then stained with fluorescence labeled anti-transfertin receptor which reacts with fetal nucleated RBCs and some activated adult lymphocytes. In three experiments, between 200–300 nucleated cells were recovered adherent to the dish. 80–88% of the cells stained for the transferrin receptor.

Example 2

Human monoclonal antibodies A6(H4CS) was prepared by fusion of heteromyeloma SHMA6 with Epstein-Barr virus transformed lymphocytes from human spleen of a Hodgkin's disease patient immunized with the J5 mutant of *E. coli* 0111-B4 (Teng et al, *Proc. Natl. Acad. Sci.*, 82:1790 (1985)).

Human monoclonal antibody 216 was prepared by fusion of uninvolved spleen lymphocytes from a patient with nodular lymphoma. The cells were incubated in vitro with LPS and fused to the heteromyeloma SHMD33 (M. Bieber and N. N. H. Teng, *Human Hybridomas*, A. J. Strelkauskas, Ed., Marcel Dekker, Inc., New York (1987).

The human monoclonal antibodies were purified on HPLC using a carboxymethyl column (BioRad, Richmond, Calif). Hybridoma supernatant containing 1% fetal calf serum (FCS) was diluted 1:4 with 20 mM sodium acetate (pH 5.5). The antibodies were eluted with 300 mM NaCl Tris buffer pH 8, dialyzed in phosphate buffered saline (PBS) and concentrated, if necessary, on a Centriprep concentrator (Amnicon, Danvets, Mass.). By SDS-PAGE analysis, the purified material was 85-90% IgM.

Both A6(H4C5) and 216 antibodies agglutinate untreated cord red blood cells. Antibody 216 agglutinates at 1-2 μg/ml and antibody A6(H4C5) agglutinates at 7-8 μg/ml. Neither antibody agglutinates adult red blood cells at >300 μg/ml. Both 216 and A6(H4C5), therefore, bind the same antigens, although they differ in their relative affinities for these antigen ligands. Following treatment with endo-β-galactosidase, the amount of antibody required for agglutination increased 5-fold. Endo-β-galactosidase specifically hydrolyzes the β1-4 linkage between Galβ1-4GlcNAc, the structural backbone of the "i" antigen. Removal of the ligand required for agglutination of cord red blood cells by antibodies 216 and A6(H4C5) with endo-β-galactosidase, but not with protease or neuraminidase, classifies these antibodies as anti-i cold agglutinin antibodies.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for separating nucleated fetal red blood cells from maternal blood, comprising
   a) applying the maternal blood to a discontinuous gradient gel having at least first, second and third layers, the first and second layers forming a first interface therebetween, and the second and third layers forming a second interface therebetween, the first layer having a density in the range of from about 1.115 to about 1.125 g/ml, the second layer having a density in the range of from about 1.105 to about 1.110 g/ml, and the third layer having a density in the range of from about 1.075 to about 1.085 g/ml;
   b) exposing the gel to a separating force field for a time sufficient to cause movement of the nucleated fetal red blood cells to the second interface;
   c) removing the nucleated fetal red blood cells from at least the second interface;
   d) contacting the removed nucleated fetal red blood cells with a solid support having bound thereto anti-i antibodies which specifically bind the epitope

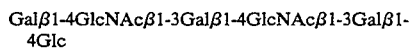

on the nucleated fetal red blood cells, wherein at least a portion of the removed nucleated fetal red blood cells are bound to the solid support through an antigen-antibody complex, thereby separating the nucleated fetal red blood cells from the maternal blood.

2. The method of claim 1, wherein the first layer has a density of 1.119 g/ml.

3. The method of claim 1, wherein the second layer has a density of 1.107 g/ml.

4. The method of claim 1, wherein the third layer has a density of 1.077 g/ml.

5. The method of claim 1, wherein the solid support is a plastic dish.

6. The method of claim 1, wherein the solid support is a magnetic bead.

7. The method of claim 1, wherein the solid support is a plastic bead.

8. A method for separating nucleated fetal red blood cells from maternal blood, and testing the separated nucleated fetal red blood cells, comprising
   a) applying the maternal blood to a discontinuous gradient gel having at least first, second and third layers, the first and second layers forming a first interface therebetween, and the second and third layers forming a second interface therebetween, the first layer having a density in the range of from about 1.115 to about 1.125 g/ml, the second layer having a density in the range of from about 1.105 to about 1.110 g/ml, and the third layer having a density in the range of from about 1.075 to about 1.085 g/ml;
   b) exposing the gel to a separating force field for a time sufficient to cause movement of the nucleated fetal red blood cells to the second interface;
   c) removing the nucleated fetal red blood cells from at least the second interface;
   d) contacting the removed nucleated fetal red blood cells with a solid support having bound thereto anti-i antibodies which specifically bind the epitope

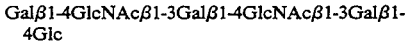

on the nucleated fetal red blood cells, wherein at least a portion of the removed nucleated fetal red blood cells are bound to the solid support through an antigen-antibody complex;
   e) warming the nucleated fetal red blood cells bound to the solid support to release the nucleated fetal red blood cells from the solid support and then probing the nucleated fetal red blood cells for a genetic defect or sex characteristic.

9. The method of claim 1, further comprising suspending the removed cells in a physiologic solution before the contacting step.

* * * * *